United States Patent [19]
Rockwood et al.

[11] Patent Number: 5,665,090
[45] Date of Patent: Sep. 9, 1997

[54] BONE CUTTING APPARATUS AND METHOD

[75] Inventors: Charles A. Rockwood, San Antonio, Tex.; Jeffrey M. Ondrla, Leesburg, Ind.; David A. Susaraba; Jon C. Serbousek, both of Warsaw, Ind.

[73] Assignee: DuPuy Inc., Warsaw, Ind.

[21] Appl. No.: 367,337

[22] PCT Filed: Sep. 9, 1992

[86] PCT No.: PCT/US92/07677

§ 371 Date: Mar. 2, 1995

§ 102(e) Date: Mar. 2, 1995

[87] PCT Pub. No.: WO94/05211

PCT Pub. Date: Mar. 17, 1994

[51] Int. Cl.$^6$ .................................................. A61B 17/56
[52] U.S. Cl. ............................. 606/80; 606/79; 606/89; 606/87; 623/22
[58] Field of Search ................... 606/79, 80, 82, 606/83, 84, 85, 86, 87, 88; 623/18, 22

[56] References Cited

U.S. PATENT DOCUMENTS

| | | |
|---|---|---|
| 3,554,192 | 1/1971 | Isberner . |
| 3,977,398 | 8/1976 | Burstein . |
| 4,239,045 | 12/1980 | Schein ............................. 606/84 X |
| 4,306,550 | 12/1981 | Forte . |
| 4,474,177 | 10/1984 | Whiteside ......................... 606/88 X |
| 4,706,659 | 11/1987 | Matthews et al. . |
| 4,751,922 | 6/1988 | DiPietropolo . |
| 4,952,213 | 8/1990 | Bowman et al. . |
| 5,002,545 | 3/1991 | Whiteside et al. ................. 606/80 |
| 5,089,004 | 2/1992 | Averill et al. . |
| 5,100,407 | 3/1992 | Conrad et al. ..................... 606/79 |
| 5,342,366 | 8/1994 | Whiteside et al. ................. 606/86 |

Primary Examiner—Guy V. Tucker
Attorney, Agent, or Firm—Barnes & Thornburg

[57] ABSTRACT

An apparatus and method for preparing a bone for receiving a prosthetic implant (74) having a body portion (75) including a plurality of fins (78, 80, 82) arranged in a predetermined pattern and a stem portion (76). The apparatus comprises a cutter (12) for cutting fin tracks in the bone (70) to guide the plurality of fins (78, 80, 82) on the implant (74) as the implant (74) is installed into the bone (70). The apparatus also includes a rod (14) coupled to the cutter (12) for locating the cutter (12) relative to an intramedullary canal of the bone (70), and a drive rod (18) and head (20) coupled to the cutter (12) for driving the cutter (12) and rod (14) into the bone (70). The rod (14) is preferably removable from the cutter (12) to permit a rod having a different size to be selectively coupled to the cutter (12) depending upon the selected size of the stem (76) of the implant (74). The apparatus also includes a collar (16) slidably coupled to the cutter (12) in a predetermined orientation. The collar (16) is configured to engage the bone (70) to determine a proper rotational position of the cutter (12) relative to the bone (70) about a longitudinal axis of the rod (14).

20 Claims, 4 Drawing Sheets

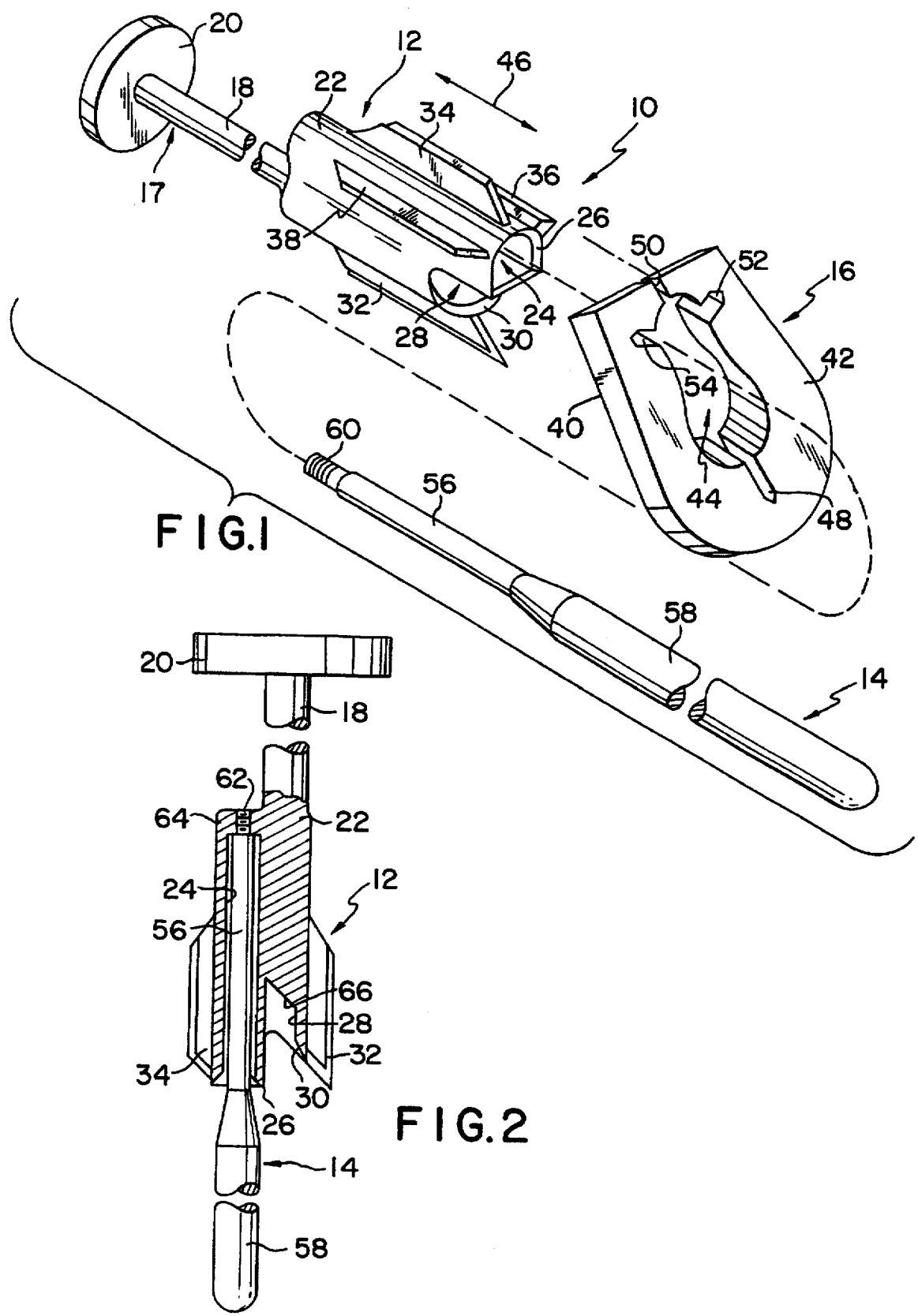

BONE CUTTING APPARATUS AND METHOD

This application is filed under 35 U.S.C. 371 based on PCT/US 92/07677 which was filed on Sep. 9, 1992.

BACKGROUND AND SUMMARY OF THE INVENTION

The present invention relates to the bone cutting apparatus and method. More particularly, the present invention relates to an apparatus and method for forming a preliminary cut in a proximal end of a bone to guide insertion and establish the position of a prosthetic implant within the bone.

It is known to install prosthetic implants into a resected end of the bone to replace the humeral head in a total shoulder arthroplasty. The humeral implant typically includes a body portion which is inserted into the resected proximal end of the humerus. A stem is coupled to the body portion. The stem passes into the intramedullary canal of the humerus. The body portion of the humeral component typically includes a plurality of fins designed to anchor the body portion of the implant within the bone and to provide rotational stability of the implant.

It is also known to provide a series of broaches having an increasing size to cut the bone from the proximal end of the humerus to permit installation of the implant. Typically, the broaches are inserted into the resected end of the humerus and removed to remove bone. The largest broach is typically sized to be slightly smaller than the implant so that the implant can be press-fit into the canal in the bone formed by the largest broach. The broaches typically include fins corresponding to the fins on the implant.

It is also known to provide a box osteotome which cuts a rectangularly shaped section from a resected bone prior to insertion of a broach. The box osteotome does not attempt to mimic the shape of the implant.

One object of the present invention is to provide a cutting apparatus having substantially the same cross sectional size and shape as the broach and implant to cut a pattern in a proximal end of a bone for guiding insertion of the broach and implant into the bone.

Another object of the present invention is to provide a modular cutting apparatus capable of preparing the proximal end of the bone for receiving a prosthetic implant which has mismatched sizes of a body portion and to a stem.

Another object of the present invention is to provide cutting apparatus which establishes the size of the implant and controls the version of the implant.

According to one aspect of the present invention, an apparatus is provided for preparing a bone for receiving a prosthetic implant which has a body portion and a stem portion. The body portion of the implant includes a plurality of fins arranged in a predetermined pattern on the body portion. The apparatus comprises a cutter including means for cutting fin tracks in the bone to guide the plurality of fins on the implant as the implant is installed into the bone. The apparatus also includes a rod coupled to the cutter for locating the cutter relative to an intramedullary canal of the bone, and means coupled to the cutter for driving the cutter and rod into the bone.

In the illustrated embodiment, the means for cutting fin tracks in the bone includes a plurality of fins formed on the cutter and arranged in the same pattern as the plurality of fins on the body portion of the implant. The fins on the cutter cut the bone in a predetermined pattern to guide installation of the implant.

According to another aspect of the invention, an apparatus is provided for preparing a bone for receiving a prosthetic implant which includes a body portion having a predetermined size and a stem portion coupled to the body portion. The stem portion of the implant has a selected one of at least two different stem sizes. The apparatus includes a cutter for cutting the bone to prepare the bone for receiving the body portion of the implant, and at least two rods having different sizes corresponding to the at least two different stem sizes. The apparatus also includes means for coupling a selected rod having a size corresponding to the selected size of the stem to the cutter. The rod is removable from the cutter to permit a rod having a different size to be selectively coupled to the cutter depending upon the selected size of the stem of the implant. The apparatus further includes means coupled to the cutter for driving the cutter and the selected rod into the bone.

In the illustrated embodiment, the cutter has a size corresponding to the predetermined size of the body portion of the implant. The body portion of the implant includes a plurality of fins arranged in a predetermined pattern on the body portion, and the cutter includes means for cutting fin tracks in the bone to guide the plurality of fins on the implant as the implant is installed into the bone.

According to yet another aspect of the invention, an apparatus is provided for preparing a surface of a bone for receiving an implant having a body portion with a predetermined shape and a stem portion. The apparatus includes a cutter for cutting the surface of the bone in a pattern corresponding to the predetermined shape of the body portion of the implant, and a rod coupled to the cutter for locating the cutter relative to the bone. The apparatus also includes a collar slidably coupled to the cutter in a predetermined orientation. The collar is configured to engage the bone to determine a proper rotational position of the cutter relative to the bone about a longitudinal axis of the rod. The apparatus further includes means coupled to the cutter for driving the cutter and rod into the bone.

In the illustrated embodiment, the body portion of the implant includes a plurality of fins arranged in a predetermined pattern on the body portion, and the cutter includes a plurality of fins arranged in the same pattern as the plurality of fins on the body portion of the implant so that the cutter cuts the bone in a shape corresponding to the shape of the body portion of the implant. The collar is formed to include a plurality of slots for receiving the plurality of fins of the cutter therethrough to align the collar in the predetermined orientation relative to the cutter.

According to still another aspect of the invention, a method is disclose for preparing a bone for receiving a prosthetic implant which includes a body portion having a predetermined size and a stem portion coupled to the body portion. The stem portion has a selected one of at least two different stem sizes. The method includes the steps of reaming an intramedullary canal of the bone with a reamer to determine the selected size of the stem, and selecting a cutter and a rod having sizes corresponding to the sizes of the body portion and stem of the prosthetic implant, respectively, from a set of cutters and rods having various sizes. The method also includes the steps of coupling the selected cutter and the selected rod together to form a cutting apparatus, and driving the cutting apparatus into the bone so that the rod enters the reamed intramedullary canal of the bone and the cutter cuts the bone in a pattern to establish the position of the implant relative to the bone. The method further includes the step of installing the implant into the bone using the cut pattern as a guide.

The illustrated method further includes the step of rotationally aligning the cutting apparatus relative to the bone prior to the driving step. The aligning step includes the step of placing a collar on the cutter in a predetermined orientation and rotating the cutting apparatus about a longitudinal axis of the rod until the collar is substantially parallel to a resected surface of the bone.

Also in the illustrated method, the installing step includes the step of inserting and removing broaches having increasing size into the bone using the pattern cut by the cutter as a guide. The installing step also includes the step of inserting the implant into a canal cut by the broaches.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

FIG. 1 is an exploded perspective view of the cutting apparatus of the present invention including the bone cutter, a rod which can be coupled to the cutter, and an alignment collar which is slidably coupled to the cutter.

FIG. 2 is a partial sectional view of the cutting apparatus of FIG. 1 after the rod has been coupled to the cutting apparatus.

DETAILED DESCRIPTION OF THE DRAWINGS

Figure 3:
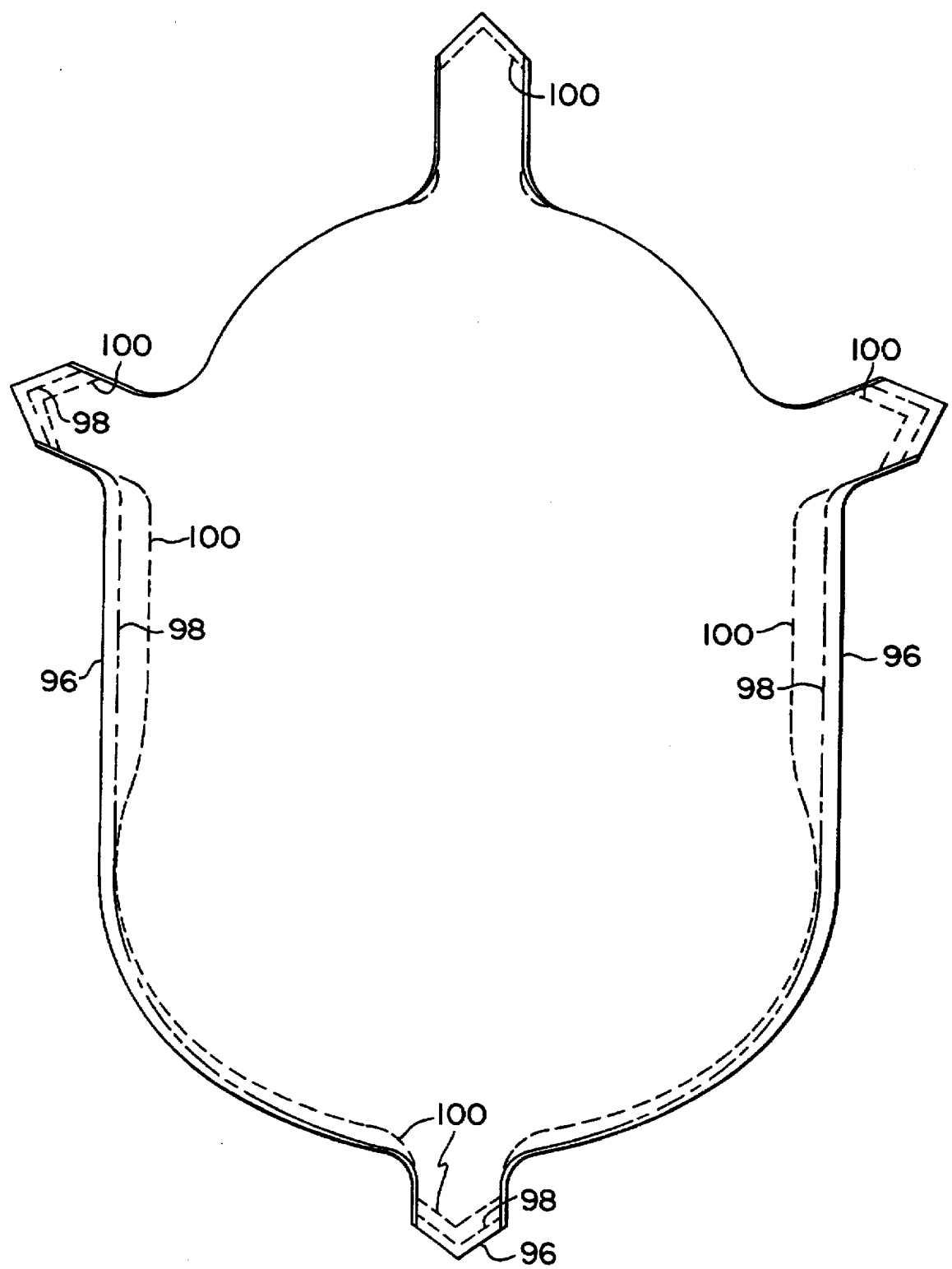
FIG. 3 is a diagrammatical view illustrating cross sections of the outer peripheries of the cutter, a broach, and a prosthetic implant.

Referring now to the drawings, FIG. 1 illustrates a modular cutting apparatus 10 of the present invention. Cutting apparatus 10 includes an osteotome or cutter 12, and intramedullary rod 14, and a collar 16.

A handle assembly 17 includes a drive rod 18 coupled to cutter 12 and a head 20. Cutter 12 includes a body 22 formed to include a first elongated aperture 24 for receiving the rod 14 therethrough to couple rod 14 to cutter 12. The outer periphery of aperture 24 is defined by cutting edge 26. Body 22 also includes a second aperture 28 defined by cutting edge 30.

Cutter 12 further includes a medial side cutting fin 32, and a lateral side cutting fin 34. Anterior/posterior cutting fins 36 and 38 are also provided. Cutting apparatus 10 is universal and designed for use on either a right side humerus or a left side humerus.

Figure 7:
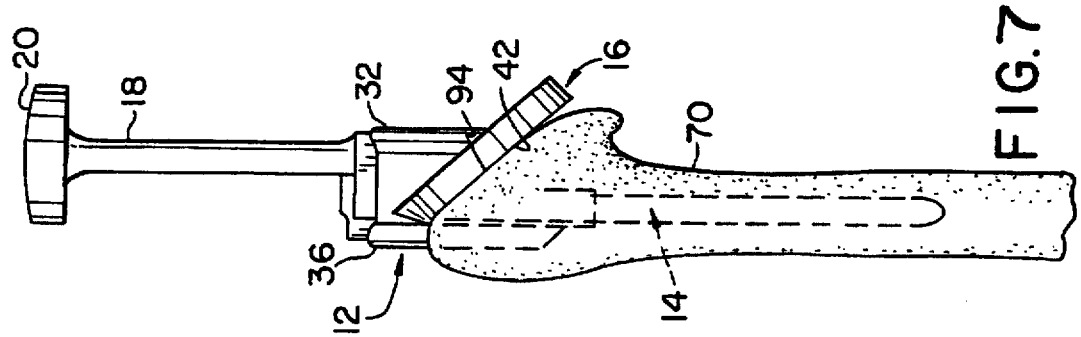
FIG. 7 is a view similar to FIG. 5, after the cutting apparatus of the present invention has been driven into the humerus.
Figure 6:
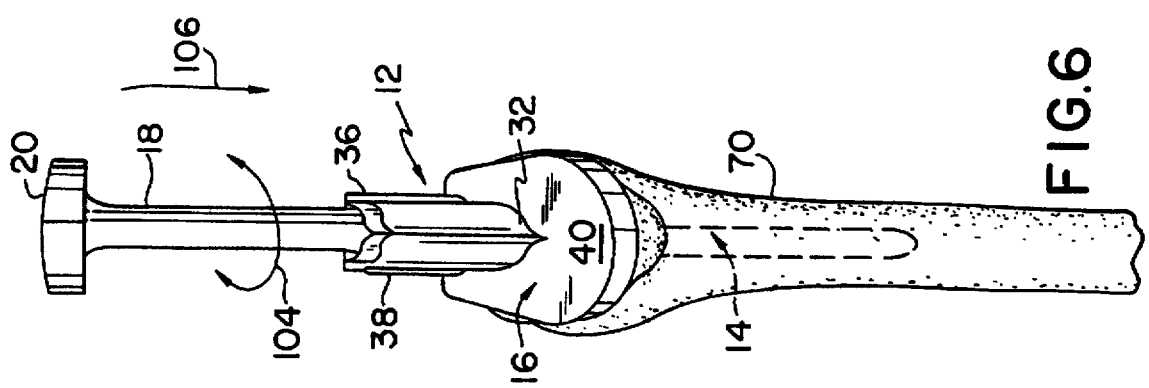
FIG. 6 is a side elevational view of FIG. 5.
Figure 5:
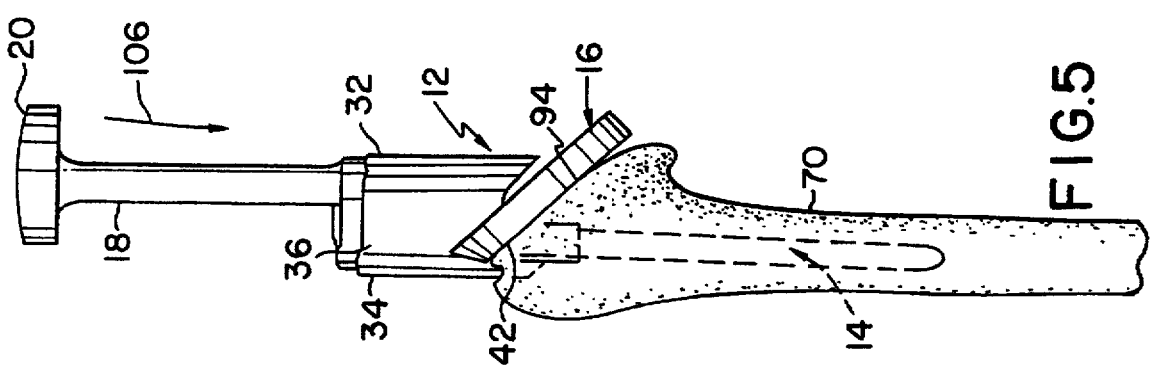
FIG. 5 illustrates the cutting apparatus of the present invention with the rod inserted into the intramedullary canal of the humerus.

Collar 16 includes a top surface 40 and a bottom surface 42. Collar 16 is formed to include an aperture 44 extending between the top and bottom surfaces 40 and 42. Aperture 44 has a configuration substantially identical to the configuration of cutter 12 so that collar 16 can slide back and forth in the direction of double headed arrow 46 over cutter 12. Collar 16 is formed to include slots 48, 50, 52 and 54 which correspond in shape to fins 32, 34, 36 an 38, respectively, of cutter 12. Aperture 44 is aligned at an angle relative to cutter 12 to approximate the angle of resected surface 94 of humerus 70. (See FIGS. 4–7) Illustratively, aperture 44 is angled at about 45 degrees relative to top and bottom surfaces 40 and 42. Therefore, collar 16 slides over cutter 12 at an angle substantially corresponding to an angle of the resected bone 94 as illustrated in FIGS. 5 and 7.

Rod 14 includes a shaft 56 having a smaller diameter than a body 58 of rod 14. An end 60 of rod 14 is threaded. As illustrated best in FIG. 2, shaft 56 of rod 14 is inserted to aperture 24 of cutter 12. Threaded section 60 of rod 14 is coupled to threads 62 formed in end portion 64 of body 22. It is understood that rod 14 does not have to be threadably coupled to cutter 12. Rod 14 can be formed so that shaft 56 engages a wall of cutter 12 defining aperture 24 to position or couple rod 14 to cutter 12 without the use of threads. Rod 14 can also be formed integrally with cutter 12, if desired. However, providing separate rods 14 and cutters 12 provides increased flexibility with fewer total parts.

As illustrated in FIG. 2, a sloped inner wall 66 is formed within aperture 28. As discussed below, cutter 12 cuts bone until wall 66 engages a top surface of the bone. After that point, bone is merely compressed as cutter 12 is driven further into the bone.

Figure 10:
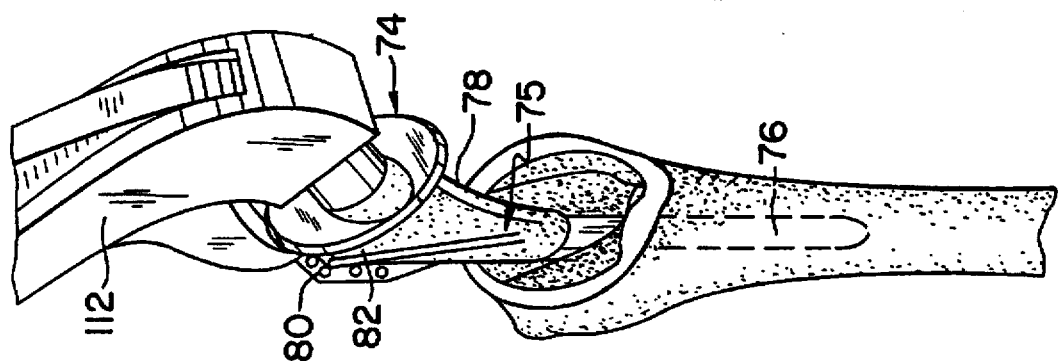
FIG. 10 illustrates insertion of a prosthetic implant into the area of the humerus cut out by the broach.
Figure 9:
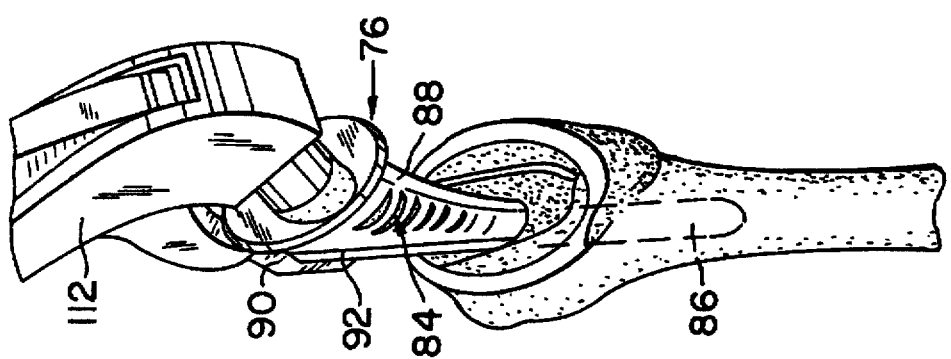
FIG. 9 is a perspective view illustrating a broach being inserted into the humerus using the pattern cut by the cutting apparatus as a guide.
Figure 8:
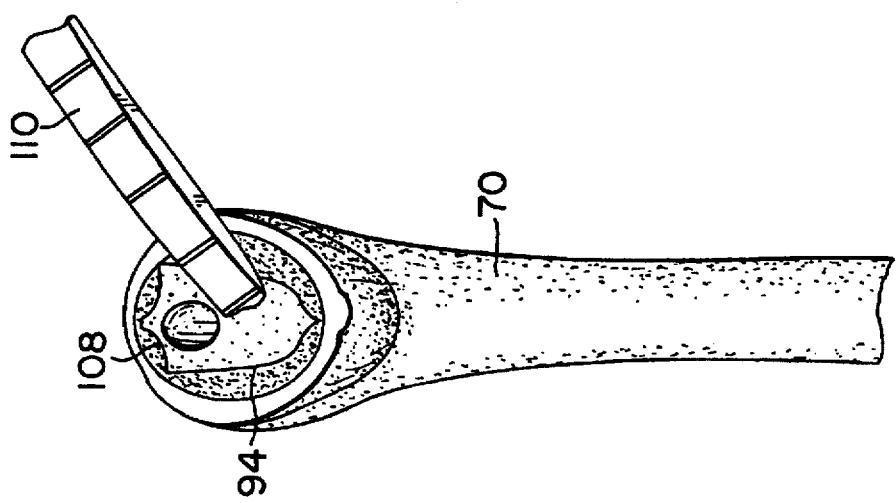
FIG. 8 is a perspective view illustrating removal of bone from an area cut by the cutting apparatus.

The prosthetic implant 74 illustrated in FIG. 10 and the broach 76 illustrated in FIG. 9 each include a plurality of fins. Implant 74 includes a body portion 75 and a stem 76. Body portion 75 of implant 74 includes a medial fin 78, a lateral fin 80, and anterior and posterior fins 82. Broach 76 includes a body portion 84 and a stem 86. Body portion 84 of broach 76 includes a medial fin 88, a lateral fin 90, and anterior and posterior fins 92. The fins on broach 76 are designed to cut humerus 70 so that the fins on implant 74 can be press-fit into the grooves cut by fins of broach 76.

Fins 32, 34, 36 and 38 of cutter 12 cut a pattern in resected end 94 of humerus 70 to provide fin tracks for the fins of broach 76. FIG. 3 illustrates the relative size and shape of cross sections taken through the cutter 12, implant 74, and broach 76. The solid line 96 illustrates the cross sectional dimension of body 75 of implant 74. Line 98 illustrates the cross sectional dimension of broach 76. Dotted line 100 illustrates the cross sectional dimension of cutter 22. Cutter 22 cuts humerus 70 in a pattern defined by dotted line 100. Therefore, cutter 12 cuts the resected end 94 of humerus 70 in a predetermined pattern corresponding in size and shape to the pattern of broach 76 and implant 74. Fins 32, 34, 36 and 38 of cutter 12 cut fin tracks in humerus 70 to guide insertion of fins 88, 90 and 92 of broach 76 and fins 78, 80 and 82 of implant 74.

FIGS. 4–10 illustrate the method in which the cutting apparatus 10 is used to prepare humerus 70 for installation of a prosthetic implant 74. For illustrative purposes, humerus 70 is discussed as the bone on which the cutting apparatus 10 is used. However, it is understood that other bones such as the femur may be cut with a similar apparatus to prepare the bone to receive an implant.

Figure 4:
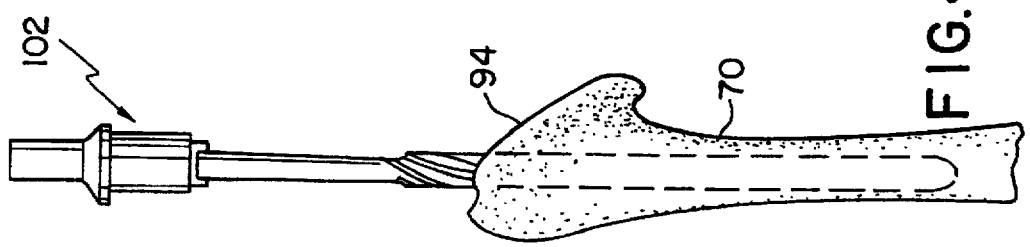
FIG. 4 is a diagrammatical view illustrating a reamer for reaming out an intramedullary canal of the humerus.

The method of the present invention begins after the humeral head has been resected from humerus 70 to form resected proximal surface 94. Once the humeral head has been removed, a reamer 102 is used to ream the medullary canal of humerus 12. Preferably, a small reamer such as 6 mm reamer is used first to make a pilot hole in the cancellous surface of the bone eccentrically and as superior as possible so reamer 102 passes down into the intramedullary canal of humerus 70 as illustrated in FIG. 4. Larger size reamers 102 are then inserted into the hole bored by the 6 mm reamer in humerus 70. For instance, an 8 mm reamer, then a 10 mm reamer, then a 12 mm reamer, then a 14 mm reamer etc. are used until reamer 102 begins to bite on cortical bone of the intramedullary canal of humerus 70. The final reamer size used determines the stem size of the prosthetic implant 74 illustrated in FIG. 9. For example, if a 10 mm reamer 102 is loose in humerus 70, and a 12 mm reamer 102 begins to bite on the cortical bone, then an implant 74 having a 12 mm stem will be used.

After a hole is reamed in humerus 70 by reamer 102, an appropriate size cutter 12 and rod 14 are selected. For example, if the last reamer 72 used was a 12 mm reamer, then a 12 mm cutter 12 and 12 mm rod 14 are also chosen. Depending on the configuration of humerus 70, a surgeon can select a different size cutter 12 if desired.

Humeral implants 74 are provided with body portions 75 and stems 76 having different or mismatched sizes. For example, implant 74 can have a 12 mm body and a 10 mm stem. In addition, it is known to provide modular implants so that the stem size and body size can be customized for each individual patient. Therefore, the present invention provides a modular cutting apparatus 10 which permits the flexibility to allow the surgeon to use a cutter 12 of one size and a rod 14 of another size. Preferably, cutters 12 having even number sizes between 6 mm and 20 mm are provided. In addition, rods 14 having even number sizes between 6 mm and 20 mm are also provided. A separate collar 16 is provided for each cutter size. Therefore, a surgeon can select different size cutters 12 and rods 14 depending upon the specific configuration of the implant 74 selected for each humerus 70. The size of rod 14 is the diameter of body 58 of rod 14. The size of cutter 12 corresponds to a body size of an implant which has a diameter at a bottom end of the body which is coupled to a stem equal to the cutter size.

After the appropriately sized cutter 12 and rod 14 are selected, rod 14 is threaded into cutter 12 to couple rod 14 to cutter 12 securely. Collar 16 is slidably coupled over cutter 12 in a predetermined orientation established by slots 48, 50, 52 and 54 of collar 16 and fins 32, 34, 36 and 38 of cutter 12. Rod 14 is then inserted into the hole in humerus 70 formed by reamer 102. Movement of rod 14 down the reamed canal prevents cutter 12 from drifting into varus as lateral side fin 34 engages cortical bone of humerus 70.

Collar 16 is used to determine proper rotation of cutter 12 about the longitudinal axis of rod 14 prior to cutting the humerus 70. When lateral side fin 34 engages a resected proximal surface 94 of humerus 70, collar 16 is moved down on cutter 12 until surface 42 of collar 16 engages resected proximal surface of 94 of humerus 70. Cutting apparatus 10 is then rotated about the longitudinal axis of rod 14 until collar 16 lies substantially flat on or parallel to resected surface 94 of humerus 70. Rotation of cutting apparatus 10 is illustrated by double headed arrow 104 in FIG. 6. Because cutting apparatus 10 establishes the position of implant 74 relative to humerus 70, it is important that the proper rotation of cutting apparatus 10 is provided. Therefore, collar 16 and cutter 12 control the version of implant 74 to prevent retroversion or anteversion of implant 74.

After cutting apparatus 10 is properly aligned with humerus 70, cutting apparatus 10 is driven into humerus 70 in the direction of arrow 106. A mallet is used to strike head 20 of cutting apparatus 10 in order to drive cutter 12 into humerus 70. Illustratively, cutter 12 is driven about 4 mm into humerus 70. FIG. 7 illustrates the position of cutting apparatus 10 after cutter 12 has been driven into humerus 70. Cutting edges 26 and 30 as well as fins 32, 34, 36 and 38 cut into the resected surface 94 of humerus 70 until surface 66 of cutter 12 engages resected surface 94.

Driving cutter 12 into humerus 70 cuts an appropriate amount of bone from humerus 70 to receive a lateral fin 90 of broach 76. In addition, cutter 12 creates the anterior, posterior and inferior fin tracks. Cutter 12 also outlines the amount of bone that will need to be removed before seating broach 76 and prosthetic implant 74. Cutter 12 mimics the shape of broach 76 and implant 74.

Cutting apparatus 10 is then removed from humerus 70. An outline or pattern 108 illustrated in FIG. 8 which is cut by cutter 12 enables a surgeon to remove a portion of the cancellous bone with a small osteotome, rongeurs, or tweezers illustrated at 110 prior to inserting broach 76.

A surgeon can inspect the size cut made by cutter 12 and determine whether a larger size cutter 12 can be used. Because the size of cutter 12 determines the size of body portion 75 of implant 74, a surgeon can use cutter 12 to determine the optimum size implant 74 to install into humerus 70.

As illustrated in FIG. 9, broaching is done in a sequential manner starting with a small broach and gradually increasing a broach 76 having substantially the same size as implant 74. The correct stem and body sizes for implant 74 have been determined from reaming with reamer 72 and utilizing the appropriate size cutter 12. A driver/extractor 112 is coupled to broach 76 and locked into position as illustrated in FIG. 9. Following the fin tracks previously established by cutting apparatus 10, broach 76 is inserted into and removed from humerus 70. Sequential broaching insures a progressive removal of bone to reduce the likelihood of cortical fracture.

It is important while broaching to maintain proper version of broach 76 by following the previously cut fin tracks established by cutter 12. As discussed above, if the proximal humerus is large in proportion to the medullary canal, a mismatched humeral implant body and stem combination is available. The mismatched combination allows for better fitting depending upon the shape of the humerus 70. The humeral implant 74 is approximately 1 mm larger than the corresponding broach size so that the press-fit of implant 74 can be obtained.

After the final broach 76 has been used on humerus 70, extractor/driver 112 is coupled to implant 74. Implant 74 is then inserted down the humeral canal cut by broach 76. Fins of the implant are aligned with the fin tracks previously created by cutting apparatus 10 and a broach 76. Implant 76 may be cemented, if desired. The humeral head (not shown) is then attached to implant 74 to complete the reconstruction of the humerus.

Although the invention has been described in detail with reference to a certain illustrated embodiment, variations and modifications exist within the scope and spirit of the invention as described and defined in the following claims.

We claim:

1. A prosthetic implant and an apparatus of preparing a bone for receiving the prosthetic implant, the implant having a body portion and plurality of fins arranged in a predetermined pattern on the body portion, apparatus comprising:

a cutter including means for cutting fin tracks in the bone to guide the plurality of fins on the implant as the implant is installed into the bone;

a rod coupled to the cutter for locating the cutter relative to an intramedullary canal of the bone; and means coupled to the cutter for driving the cutter and rod into the bone.

2. The apparatus of claim 1, further comprising a collar slidably coupled to the cutter in a predetermined orientation, the collar being configured to engage the bone to determine a proper rotational position of the cutter relative to the bone about a longitudinal axis of the rod.

3. The apparatus of claim 1, wherein the rod is removable from the cutter to permit various sizes of rods to be selectively coupled to the cutter corresponding to a predetermined size of the stem of the implant.

4. The apparatus of claim 1, wherein the body portion of the implant has a predetermined size and the cutter has a size corresponding to the predetermined size of the body portion of the implant.

5. The apparatus of claim 1, wherein the means for cutting fin tracks in the bone includes a plurality of fins formed on the cutter and arranged in the same pattern as the plurality of fins on the body portion of the implant.

6. The apparatus of claim 5, further comprising a collar slidably coupled to the cutter, the collar being formed to include a plurality of slots for receiving the plurality of fins of the cutter therethrough to align the collar in a predetermined orientation relative to the cutter, the collar being configured to engage the bone to determine a proper rotational position of the cutter relative to the bone about a longitudinal axis of the rod.

7. A prosthetic implant and an apparatus for preparing a bone for receiving the prosthetic implant which prosthetic implant includes a body portion having a predetermined size and a stem portion coupled to the body portion, and with the body portion having a plurality of fins extending outwardly therefrom and with the stem portion having a selected one of at least two different stem sizes, the apparatus comprising:

a cutter for cutting the bone including means for cutting fin tracks into the bone to prepare the bone for receiving the body portion of the implant;

at least two rods having different sizes corresponding to the at least two different stem sizes;

means for coupling a selected rod to the cutter, the selected rod having a size corresponding to the selected size of the stem, the rod being removable from the cutter to permit a rod having a different size to be selectively coupled to the cutter depending upon the selected size of the stem of the implant; and means coupled to the cutter for driving the cutter and the selected rod into the bone.

8. The apparatus of claim 7, wherein the cutter has a size corresponding to the predetermined size of the body portion of the implant.

9. The apparatus of claim 7, wherein the fins are arranged in a predetermined pattern on the body portion, and the means for cutting fin tracks are arranged in the same pattern as the plurality of fins on the body portion of the implant so that the cutter cuts the bone in a shape corresponding to the shape of the body portion of the implant.

10. The apparatus of claim 7, further comprising a collar slidably coupled to the cutter in a predetermined orientation, the collar being configured to engage the bone to determine a proper rotational position of the cutter relative to the bone about a longitudinal axis of the rod.

11. An apparatus for preparing a surface of a bone for receiving an implant having a body portion with a predetermined shape including fin portions extending outwardly thereof and a stem portion, the apparatus comprising:

a cutter for cutting the surface of the bone in a pattern corresponding to the predetermined shape of the body portion as well as cutting fin tracks for receiving the implant;

a rod coupled to the cutter for locating the cutter relative to the bone;

a collar with an opening therethrough slidably coupled to the cutter in a predetermined orientation, the collar being configured to engage the bone to determine a proper rotational position of the cutter relative to the bone about a longitudinal axis of the rod; and means coupled to the cutter for driving the cutter and rod into the bone.

12. The apparatus of claim 11, wherein the stem of the implant has a predetermined size, and the rod is removable from the cutter to permit various sizes of rods to be selectively coupled to the cutter depending upon the predetermined size of the stem of the implant.

13. The apparatus of claim 12, wherein the cutter has a size corresponding to a predetermined size of the body portion of the implant.

14. An apparatus for preparing a surface of a bone for receiving an implant having a body portion with a predetermined shape and a stem portion, the apparatus comprising:

a cutter for cutting the surface of the bone in a pattern corresponding to the predetermined shape of the body portion of the implant;

a rod coupled to the cutter for locating the cutter relative to the bone;

a collar slidably coupled to the cutter in a predetermined orientation, the collar being configured to engage the bone to determine a proper rotational position of the cutter relative to the bone about a longitudinal axis of the rod;

means coupled to the cutter for driving the cutter and rod into the bone;

wherein the body portion of the implant includes a plurality of fins arranged in a predetermined pattern on the body portion, and the cutter includes a plurality of fins arranged in the same pattern as the plurality of fins on the body portion of the implant so that the cutter cuts the bone in a shape corresponding to the shape of the body portion of the implant; and wherein the collar is formed to include a plurality of slots for receiving the plurality of fins of the cutter therethrough to align the collar in the predetermine orientation relative to the cutter.

15. The apparatus of claim 11, wherein the collar is aligned at a predetermined angle relative to the cutter.

16. The apparatus of claim 15, wherein the predetermined angle is about 45 degrees.

17. A method of preparing a bone for receiving a prosthetic implant which includes a body potion having a predetermined size and a stem portion coupled to the body portion, the body portion having a plurality of fins extending outwardly therefrom and the stem portion having a selected one of at least two different stem sizes, the method comprising the steps of:

reaming an intramedullary canal of the bone with a reamer to determine the selected size of the stem;

selecting a cutter and a rod having sizes corresponding to the sizes of the body portion with its fins and the stem of the prosthetic implant, respectively, from a set of cutters and rods having various sizes;

coupling the selected cutter and the selected rod together to form a cutting apparatus;

driving the cutting apparatus into the bone so that the rod enters the reamed intramedullary canal of the bone and the cutter cuts the bone in a pattern to establish the position of the body and fins relative to the bone; and installing the implant into the bone using the cut pattern as a guide.

18. The method of claim 17, further comprising the step of rotationally aligning the cutting apparatus relative to the bone prior to the driving step.

19. The method of claim 17, wherein the installing step includes the steps of inserting and removing broaches having increasing size into the bone using the pattern cut by the cutter as a guide and then inserting the implant into a canal cut by the broaches.

20. A method of preparing a bone for receiving a prosthetic implant which includes a body portion having a predetermined size and a stem portion coupled to the body portion, the stem portion having a selected one of at least two different stem sizes the method comprising the steps of:

reaming an intramedullary canal of the bone with a reamer to determine the selected size of the stem;

selecting a cutter and a rod having sizes corresponding to the sizes of the body portion and stem of the prosthetic implant, respectively, from a set of cutters and rods having various sizes;

coupling the selected cutter and the selected rod together to form a cutting apparatus;

driving the cutting apparatus into the bone so that the rod enters the reamed intramedullary canal of the bone and the cutter cuts the bone in a pattern to establish the position of the implant relative to the bone;

installing the implant into the bone using the cut pattern as a guide;

further comprising the step of rotationally aligning the cutting apparatus relative to the bone prior to the driving step; and wherein the aligning step includes the step of placing a collar on the cutter in a predetermined orientation and rotating the cutting apparatus about a longitudinal axis of the rod until the collar is substantially parallel to a resected surface of the bone.

* * * * *

UNITED STATES PATENT AND TRADEMARK OFFICE
CERTIFICATE OF CORRECTION

PATENT NO. : 5,665,090
DATED : September 9, 1997
INVENTOR(S) : Charles A. Rockwood, et al It is certified that error appears in the above-identified patent and that said Letters Patent is hereby corrected as shown below:

On the title page, item [73], change "DePuy Inc." to --DePuy Orthopaedics, Inc.--.

Signed and Sealed this

Seventh Day of July, 1998

*Attest:*

BRUCE LEHMAN

*Attesting Officer*      *Commissioner of Patents and Trademarks*